United States Patent
Santilli et al.

(10) Patent No.: US 6,441,019 B2
(45) Date of Patent: Aug. 27, 2002

(54) CYCLOCARBAMATE AND CYCLIC AMIDE DERIVATIVES

(75) Inventors: Arthur A. Santilli, Havertown; Andrew Q. Viet, Upper Darby; Puwen Zhang, Audubon; Andrew Fensome, Wayne, all of PA (US); Jay E. Wrobel, Lawrenceville, NJ (US); James P. Edwards, San Diego, CA (US); Todd K. Jones, Solana Beach, CA (US); Christopher M. Tegley, Thousand Oaks, CA (US); Lin Zhi, San Diego, CA (US)

(73) Assignees: Wyeth, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/906,875

(22) Filed: Jul. 17, 2001

Related U.S. Application Data

(62) Division of application No. 09/552,036, filed on Apr. 19, 2000.
(60) Provisional application No. 60/183,015, filed on May 4, 1999, now abandoned.

(51) Int. Cl.$^7$ ..................... A61K 31/535; C07D 498/04
(52) U.S. Cl. ..................... 514/409; 548/411; 548/453; 514/421
(58) Field of Search ................ 548/411, 453; 514/409, 421

(56) References Cited

U.S. PATENT DOCUMENTS

| | | | |
|---|---|---|---|
| 3,635,964 A | 1/1972 | Skorca | 260/247.1 |
| 3,917,592 A | 11/1975 | Kobzina | 260/244 |
| 4,093,730 A | 6/1978 | Butti | 424/270 |
| 4,440,785 A | 4/1984 | Walsh | 424/317 |
| 4,666,913 A | 5/1987 | Kuhla | 514/259 |
| 4,670,566 A | 6/1987 | Walsh | 548/485 |
| 4,721,721 A | 1/1988 | Kuhla | 514/312 |
| 4,822,794 A | 4/1989 | Spada | 514/230.5 |
| 4,831,027 A | 5/1989 | Narr | 514/212 |
| 4,853,473 A | 8/1989 | Fischer | 547/326 |
| 5,007,952 A | 4/1991 | Kume | 71/73 |
| 5,171,851 A | 12/1992 | Kim | 544/50 |
| 5,414,088 A | 5/1995 | von der Saal | 546/158 |
| 5,453,516 A | 9/1995 | Fischer | 548/543 |
| 5,475,020 A | 12/1995 | Johnson | 514/414 |
| 5,521,166 A | 5/1996 | Grubb | 514/170 |
| 5,681,817 A | 10/1997 | Hodgen | 514/12 |
| 5,688,808 A | 11/1997 | Jones | 514/285 |
| 5,688,810 A | 11/1997 | Jones | 514/311 |
| 5,693,646 A | 12/1997 | Jones | 514/285 |
| 5,693,647 A | 12/1997 | Jones | 514/285 |
| 5,696,127 A | 12/1997 | Jones | 514/285 |
| 5,696,130 A | 12/1997 | Jones | 514/291 |
| 5,696,133 A | 12/1997 | Jones | 514/314 |
| 5,719,136 A | 2/1998 | Chwalisz | 514/170 |
| 5,733,902 A | 3/1998 | Schneider | 514/177 |
| 5,808,139 A | 9/1998 | Pathirana | 560/138 |
| 5,874,430 A | 2/1999 | Christ | 514/229.8 |
| 6,077,840 A | 6/2000 | Kurihara | 514/232.8 |

FOREIGN PATENT DOCUMENTS

| | | |
|---|---|---|
| DE | 3633861 | 4/1988 |
| DE | 4330234 | 3/1995 |
| EP | 022317 | 1/1981 |
| EP | 208510 | 1/1987 |
| EP | 311135 | 4/1989 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63112584 | 5/1998 |

(List continued on next page.)

OTHER PUBLICATIONS

Horwitz et al., "Progestin, progesterone receptors, and breast cancer", publisher: Birkhaeuser, Boston, Mass., ed Vedeckis, p. 283–306 (1996).*

(List continued on next page.)

Primary Examiner—Mukund J. Shah
Assistant Examiner—Hong Liu
(74) Attorney, Agent, or Firm—Howson and Howson

(57) ABSTRACT

This invention provides compounds of the formula:

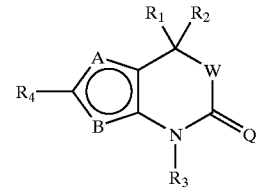

wherein A and B are independent substituents selected from S, CH or N; provided that when A is S, B is CH or N; and when B is S, A is CH or N; and A and B cannot both be CH; and when A and B both equal N, one N may be optionally substituted with an $C_1$ to $C_6$ alkyl group; $R_1$ and $R_2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$; or $R^1$ and $R^2$ are fused to form optionally substituted 3 to 8 membered spirocyclic alkyl, alkenyl or heterocyclic ring, the heterocyclic ring containing one to three heteroatoms selected from the group of O, S and N; or pharmaceutically useful salts thereof. The compounds of this invention are useful as agonists and antagonists of the progesterone receptor and in methods of inducing contraception and in the treatment or prevention of benign or malignant neoplastic diseases.

10 Claims, No Drawings

FOREIGN PATENT DOCUMENTS

| WO | WO86/03749 A1 | 7/1986 |
|---|---|---|
| WO | WO91/04974 A1 | 4/1991 |
| WO | WO91/06545 A1 | 5/1991 |
| WO | WO93/12085 A1 | 6/1993 |
| WO | WO94/14434 A1 | 7/1994 |
| WO | WO94/29272 A1 | 12/1994 |
| WO | WO95/11013 A1 | 4/1995 |
| WO | 4344463 | 6/1995 |
| WO | WO95/20389 A1 | 8/1995 |
| WO | WO95/20972 A1 | 8/1995 |
| WO | WO95/33746 A1 | 12/1995 |
| WO | WO96/15794 A1 | 5/1996 |
| WO | WO96/19458 A1 | 6/1996 |
| WO | WO96/19997 A1 | 7/1996 |
| WO | WO97/13767 A1 | 4/1997 |
| WO | WO97/49407 A1 | 12/1997 |
| WO | WO98/14436 A1 | 4/1998 |
| WO | WO98/27059 A1 | 6/1998 |
| WO | WO98/55116 A1 | 12/1998 |
| WO | WO99/10325 A1 | 3/1999 |
| WO | WO99/11264 A1 | 3/1999 |
| WO | WO99/15500 A1 | 4/1999 |
| WO | WO99/44608 A1 | 9/1999 |

OTHER PUBLICATIONS

Wensbo et al. Indole–3–acetic acids and hetero analogues by one pot synthesis including Heck cylcisation, Tetrahedron 51(37) 10323–10342, 1995.*

R. Evans, "The Steroid and Thyroid Hormone Receptor Superfamily", Science, 240:889 (May 13, 1988).

A. Ulmann et al, "Clinical Uses of Mifepristone (MFP)", Ann. N.Y. Acad. Sci., 261:248 (Jun. 12, 1995).

R. Kekkonen et al, "Sequential Regiment of the Antiprogesterone RU486 and Synthetic Progestin for Contraception", Fertility and Sterility, 60(4):610 (Oct., 1993).

K. Horwitz et al, "Progestin, Progesterone Receptors, and Breast Cancer", Horm. Cancer, publisher: Birkhaeuser, Boston, Mass., ed. Vedeckis, pp. 283–306 (1996) (abstract only).

A. Murphy et al, "Regression of Uterine Leiomyomata in Response to the Antiprogesterone RU486", J. Clin. Endo. Metab., 76(2):513 (Feb., 1993).

L. Kettel et al, "Endocrine Responses to Long–Term Administation of the Antiprogesterone RU486 in Patients with Pelvic Endometriosis", Fertility and Sterility, 56(3):402 (Sep., 1991).

H. Michna et al, "Differentiation Therapy with Progesterone Antagonists", Ann. N.Y. Acad. Sci., 761:224 (Jun., 1995).

L. Zhi et al, "5–Aryl–1,2–Dihydrochromeno[3,4–f]quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High–Affinity Ligands with Selectivity for Bone Cell Progesterone Receptors", J. Med. Chem., 38:4880 (Dec. 8, 1995).

K. Perlman et al, "20–Oxopregnacalciferols: Vitamin D Compounds that Bind the Progesterone Receptor", Tet. Letters, 35(15)2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effects of Brofoxine, A New Anxiolytic on Experimentally Induced Conflict in Rats", Proc. West. Pharmacol. Soc., 21:51–55 (1978).

B. Singh et al, "Novel cAMP PDE III Inhibitor" Imidazo [4,5–b]pyridin–2(3H)–ones and Thiazolo[4,5–b] pyridin–2(3H)–ones and their Analogs, J. Med. Chem., 37:248 (Jan. 21, 1994).

A. Andreani et al, "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7–Chlor–5–phenyl–2–thioxo–1H–2,3–Dihydro–1,3,4–benzotriazepinen", Pharmazie, 37(10):714–717 (19820.

E. Barengolts et al, "Progesterone Antagonist RU486 has Bone–Sparing Effects in Ovariectomized Rats", Bone, 17(1):21 (Jul., 1995).

E. Gromachevskaya et al, "Studies of 4H–3, 1–Benzoxazines", Chem. Heterocycl. Cmpds., 33(10):1209–1214 (1997).

D. Chiarino et al, "2,1–Benzisothiazoline 2,2–Dioxide and Derivatives", J. Heterocycl. Chem., 23(6):1645–1649 (Nov.-Dec., 1986).

A. Turck et al, "On the Metabolism of 3–Substituted and 3,6–Disubstituted Pyridazines", Tetrahedron, 49(3):599–606 (1993).

V. Kumar et al, "Synthesis of 7–Azaindole and 7–Azaoxindole Derivatives through a Palladium–Catalyzed CrossCoupling Reaction", J. Org. Chem., 57(25):6995–6998 (1992).

P. Canonne et al, "Spirocyclization of 1–(o–Aminophenyl-)cycloalkanols and 1–(2'–Amino–3'–pyridinyl)cycloalkanols", J Heterocyclic Chem., 26:113 (Jan.–Feb., 1989).

M–C. Forest et al, "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", J. Med. Chem., 35:163–172 (Jan., 1992).

D. Combs et al, "Heteroatom Analogues of Bemoradan: Chemistry and Cardiotonic Activity of 1,4–Benzothiazinylpyridazinones", J. Med. Chem., 35:172–176 (Jan., 1992).

Kurihari et al., "Synthesis of (±)–PF1092A, B, and C; New Nonsteroidal Progesterone Receptor Ligands", J. Antibiotics, 50(4):360 (Apr., 1997).

A. Kende et al., "Regioselective C–3 Alkylation of Oxindole Dianion", Synth. Commun. 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", J. Med. Chem., 37:2347–2444 (Jul. 22, 1994).

J. Edwards et al., "5–Aryl–1,2–Dihydro–5H–Chromeno[3, 4–f]Quinolines as Potent, Orally Active, Nonsteroidal Progesterone Receptor Agonists: The Effect of D–Ring Substituents", J. Med. Chem., 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850.

Derwent WPI abstract, F. Arndt et al., "New Heterocycle substituted Benzo–Fused Azine and Azole Derivatives—Useful as Selective Herbicides for Pre or Post–Emergence Application", EP 311135.

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

V. Mamaev et al., "Synthesis of 4H–Thieno [3,2–B] Pyrrol–5(6H)–One" Bulletin of the Academy of Sciences on the USSR. Division of Chemical Science, US, Consultants Bureau. New York. vol. 9, p. 1549–1553, (1966).

Derwent WPI Abstract, K. Chwalisz et al. "Female Contraceptive Method Comprises Gestation Treatment with Intermittent Progesterone Antagonist Administration.", DE 4,330,234.

Derwent WPI Abstract, K. Chwalisz et al. "Contraceptive Pack for Implantation Inhibition—Contains Competitive Progesterone Antagonist and Gestagen for Sequential Oral Administration.", DE 4,344,463.

K. Kolasa et al., "Preliminary Pharmacological Studies of the Central Action of Phenyl and Piperidinomethyl Derivatives of 2–Benzoxazolone", Chemical Abstracts, vol. 99, No. 1, Abst. No. 157a (Jul. 4, 1983).

N. Meanwell et al., "Regiospecific Functionalization of 1,3–dihydro–2H–Benzimidazol–2–One and Structurally Related Cyclic Urea Derivatives", J. Organic Chem., 60(6):1565–82 (Mar. 24, 1995).

B. Singh et al., "An Efficient and Novel Synthesis of Fused Thiazol–2(3H)–ones" Heterocycles, 36(1):133–134, p. 136, compounds 16a, 18a (Jan. 1993).

G. Vernin et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6– et furyl–6–ethyl–2–benzothiazoles, des sels quaternaires et des spiropyrannes correspondants", Helvetica Chimica Acta, 62(1/3):21–30 (Jan. 24, 1979).

P. Zhang et al, "Cyclocarbamate Derivatives as Progesterone Receptor Modulators", U. S. Application No. 09/552,633, filed Apr. 19, 2000.

A. Fensome et al, "Indoline Derivatives", U. S. Application No. 09/552,632, filed Apr. 19, 2000.

J. Ullrich et al, "3,3–Substituted Indoline Derivatives", U. S. Application No. 09/552,352, filed Apr. 19, 2000.

A. Fensome et al, "Thio–Oxindole Derivatives", U. S. Application No. 09/552,033, filed Apr. 19, 2000.

P. Zhang et al, "Cyclothiocarbamate Derivatives as Progesterone Receptor Modulators", U. S. Application No. 09/552,354, filed Apr. 19, 2000.

P. Zhang et al, "Benzimidazolones and Analogues", U. S. Application No. 09/552,546, filed Apr. 19, 2000.

M. Collins et al, "2,1–Benzisothiazoline 2,2–Dioxides", U. S. Application No. 09/552,630, filed Apr. 19, 2000.

P. Zhang et al, "Cyclic Urea and Cyclic Amide Derivatives", U. S. Application No. 09/552,356, filed Apr. 19, 2000.

P. Zhang et al, "Quinazolinone and Benzoxazine Derivatives as Progesterone Receptor Modulators", U. S. Application No. 09/552,629, filed Apr. 19, 2000.

M. Collins et al, "Cyanopyrroles", U. S. Application No. 09/552,544, filed Apr. 19, 2000.

G. Grubb et al, "Cyclic Regimens Using Quinazolinone and Benzoxazine Derivatives", U. S. Application No. 09/552,357, filed Apr. 19, 2000.

A. Santilli et al, "Cyclocarbamate and Cyclic Amide Derivatives", U. S. Application No. 09/552,036, filed Apr. 19, 2000.

G. Grubb et al, "Cyclic Regimens Using Cyclic Urea and Cyclic Amide Derivatives", U. S. Application No. 09/552,037, filed Apr. 19, 2000.

G. Grubb et al, "Combination Regimens Using Progesterone Receptor Modulators", U. S. Application No. 09/552,350, filed Apr. 19, 2000.

G. Grubb et al, "Combination Regimens Using 3,3–Substituted Indoline Derivatives", U. S. Application No. 09/552,631, filed Apr. 19, 2000.

G. Grubb et al, "Combination Therapies Using Benzimidazolones", U. S. Application No. 09/552,355, filed Apr. 19, 2000.

G. Grubb et al, "Cyclic Regimens Using Cyclocarbamate and Cyclic Amide Derivatives", U. S. Application No. 09/552,545, filed Apr. 19, 2000.

G. Grubb et al, "Cyclic Regimens Utilizing Indoline Derivatives", U. S. Application No. 09/552,358, filed Apr. 19, 2000.

G. Grubb et al, "Cyclic Regimens Using 2,1–Benzisothiazoline 2,2–Dioxides", U. S. Application No. 09/552,038, filed Apr. 19, 2000.

L. Zhi et al, "Tetracyclic Receptor Modulator Compounds and Methods", U. S. Application No. 09/552,353, filed Apr. 19, 2000.

* cited by examiner

CYCLOCARBAMATE AND CYCLIC AMIDE DERIVATIVES

CROSS-REFERENCE TO RELATED APPLICATIONS

This application is a divisional of U.S. patent application Ser. No. 09/552,036, filed Apr. 19, 2000, now U.S. Pat. No. 6,306,851, which claims the benefit of U.S. Patent Application No. 60/183,015, filed May 4, 1999, now abandoned.

FIELD OF THE INVENTION

This invention relates to compounds that act as agonists and antagonists of the progesterone receptor, their preparation, and utility.

BACKGROUND OF THE INVENTION

Intracellular receptors (IR) form a class of structurally related genetic regulators known as "ligand dependent transcription factors" (R. M. Evans, Science, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex then translocates to the nucleus of the cell where it binds to a specific gene or genes present in the cell's DNA. Once bound to a specific DNA sequence the complex modulates the production of the MRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, typically in the presence of an ER agonist. ER agonists are used to treat the symptoms of menopause, but have been associated with a proliferative effect on the uterus (in non-hysterectomized women) which can lead to an increased risk of uterine cancers. Co-administration of a PR agonist reduces or ablates that risk.

PR antagonists may also be used in contraception. In this context they may be administered alone (Ulmann, et al, Ann. N Y. Acad Sci., 261, 248, 1995), in combination with a PR agonist (Kekkonen, et al, Fertility and Sterility, 60, 610, 1993) or in combination with a partial ER antagonist such as tamoxifen (WO 96/19997 A1 Jul. 4, 1996).

PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, J. Clin. Endo. Metab., 76, 513, 1993) and endometriosis (Kettel, et al, Fertility and Sterility, 56, 402, 1991).

PR antagonists may also be useful in hormone replacement therapy for post-menopausal patients in combination with a partial ER antagonist such as tamoxifen (U.S. Pat. No. 5,719,136). PR antagonists such as Mifepristone have also been shown to have bone sparing effects in rodents, and as such may be useful in the treatment of osteoporosis associated with the menopause (Barengolts, et al, Bone, 17, 21, 1995).

PR antagonists, such as mifepristone and onapristone, have been shown to be effective in a model of hormone dependent prostate cancer, which may indicate their utility in the treatment of this condition in men (Michna, et al, Ann. N. Y. Acad. Sci., 761, 224, 1995).

Jones, et al, (U.S. Pat. No. 5,688,810) described the PR antagonist dihydroquinoline 1.

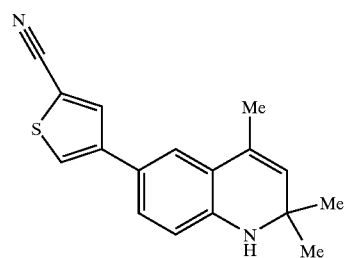

Jones, et al, described the enol ether 2 (U.S. Pat. No. 5,693,646) as a PR ligand.

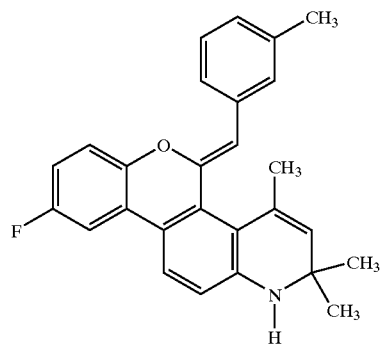

Jones, et al, described compound 3 (U.S. Pat. No. 5,696,127) as a PR ligand.

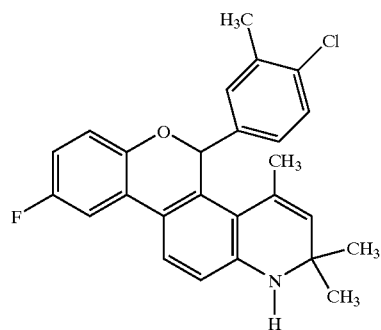

Zhi, et al, described lactones 4, 5 and 6 as PR antagonists (J. Med. Chem., 41, 291, 1998).

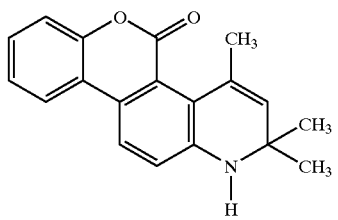

4

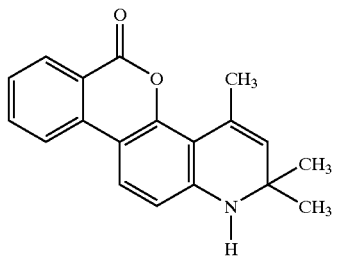

5

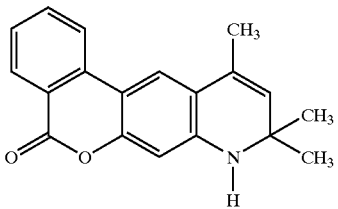

6

Zhi, et al, described the ether 7 as a PR antagonist (J. Med. Chem., 41, 291, 1998).

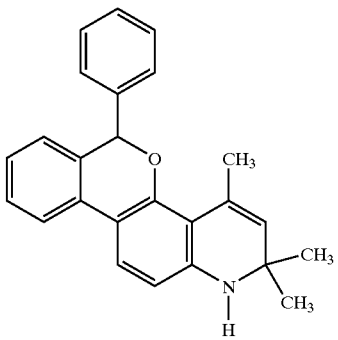

7

Combs, et aL, disclosed the aide 8 as a ligand for the PR (J. Med. Chem., 38, 4880, 1995).

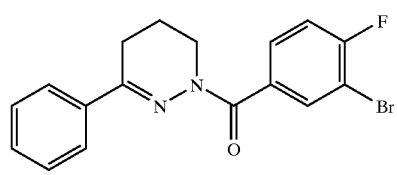

8

Perlman, et al, described the vitamin D analog 9 as a PR ligand (Tet. Letters, 35, 2295, 1994).

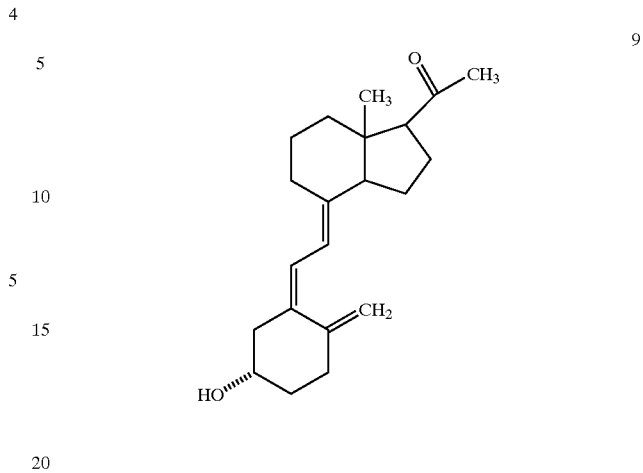

9

Hamann, etal, described the PR antagonist 10 (Ann. N.Y Acad Sci., 761, 383, 1995).

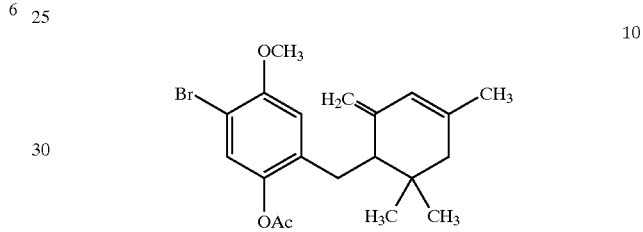

10

Chen, et al, described the PR antagonist 11 (Chen, et al, POI-37, 16$^{th}$ Int. Cong. Het. Chem., Montana, 1997).

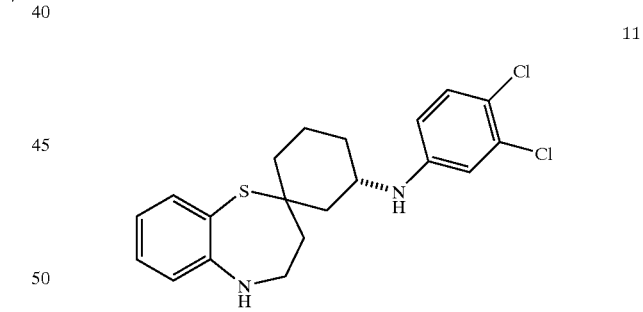

11

Kurihari, et. al., described the PR ligand 12 (J. Antibiotics, 50, 360, 1997).

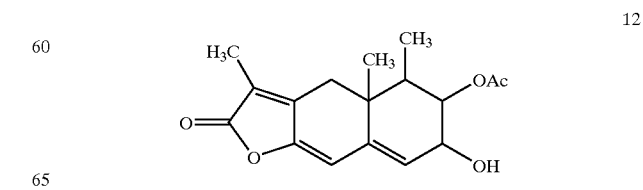

12

DESCRIPTION OF THE INVENTION

This invention provides compounds of Formula I:

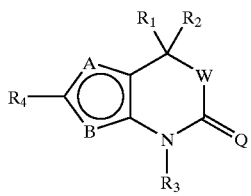

wherein:

A and B are independent substituents selected from S, CH or N;
Provided that when A is S, B is CH or N; provided that when B is S, A is CH or N;
and A and B cannot both be CH;
and when A and B both equal N, one N may be optionally substituted with an $C_1$ to $C_6$ alkyl group;

$R^1$ and $R_2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

or $R^1$ and $R^2$ are fused to form:
  a) an optionally substituted 3 to 8 membered spirocyclic alkyl ring, preferably a 3 to 6 membered spirocyclic alkyl ring; or
  b) an optionally substituted 3 to 8 membered spirocyclic alkenyl ring, preferably a 3 to 6 membered spirocyclic alkenyl ring; or
  c) an optionally substituted 3 to 8 membered spirocyclic ring containing one to three heteroatoms selected from O, S and N, preferably a 3 to 6 membered spirocyclic ring containing one to three heteroatoms;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted C, to $C_6$ alkenyl, alkynyl, or substituted alkynyl, or $COR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is a trisubstituted benzene ring containing the substituents X, Y and Z as shown below,

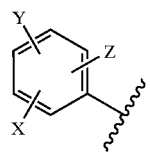

X is selected from halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, CORD, $OCOR^D$, or $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent independently selected from H, halogen, CN, $NO_2$, $C_1$ to $C_3$ alkoxy, $C_1$ to $C_3$ alkyl, or $C_1$ to $C_3$ thioalkyl; or $R^4$ is a five or six membered ring with 1, 2, or 3 heteroatoms from the group including O S, SO, $SO_2$ or $NR^5$ and containing one or two independent substituents from the group including H, halogen, CN, $NO_2$ and $C_1$ to $C_3$ alkyl, $C_1$ to $C_3$ alkoxy, $C_1$ to $C_3$ aminoalkyl, $COR^F$, or $NR^G COR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H, or $C_1$ to $C_3$ alkyl;

Q is O, S, $NR^6$, or $CR^7 R^8$;

$R^6$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2 CF_3$;

$R^7$ and $R^8$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, or CN $CO_2 R^9$;

$R^9$ is $C_1$ to $C_3$ alkyl; or $CR^7 R^8$ may comprise a six membered ring of the structure below:

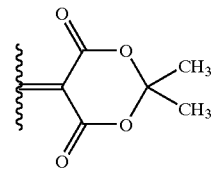

W is O or a chemical bond
or a pharmaceutically acceptable salt thereof.

Among the preferred compounds of this invention are those of Formula I wherein:

A and B are independent substituents S, CH or N, provided that when A is S, B is CH or N; and
when B is S, A is CH or N; and
A and B cannot both be CH; and
when A and B both equal N, one N may be optionally substituted with an $C_1$ to $C_6$ alkyl group;

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

or $R^1$ and $R^2$ are fused to form:
  a) an optionally substituted 3 to 8 membered spirocyclic alkyl ring; or
  b) an optionally substituted 3 to 8 membered spirocyclic alkenyl ring; or
  c) an optionally substituted 3 to 8 membered spirocyclic ring containing one to three heteroatoms selected from the group of O, S and N;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, or $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is a trisubstituted benzene ring containing the substituents X, Y and Z as shown below:

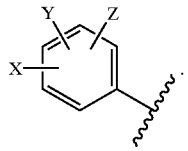

X is taken from the group including halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5-membered heterocyclic ring containing 1 to 3 heteroatoms, $COR^D$, $OCOR^D$, or $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ amninoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents taken from the group including H, halogen, CN, $NO_2$, $C_1$ to $C_3$ alkoxy, $C_1$ to $C_3$ alkyl, or $C_1$ to $C_3$ thioalkyl; or $R^4$ is a five or six membered ring with 1, 2, or 3 heteroatoms from the group including O, S, SO, $SO_2$ or $NR^5$ and containing one or two independent substituents from the group including H, halogen, CN, $NO_2$ and $C_1$ to $C_3$ alkyl, or $C_1$ to $C_3$ alkoxy;

$R^5$ is H or $C_1$ to $C_3$ alkyl;

Q is O, S, $NR^6$, or $CR^7R^8$;

$R^6$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R^7$ and $R^8$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, or CN $CO_2R^9$;

$R^9$ is $C_1$ to $C_3$ alkyl; or $CR^8R^9$ comprise a six membered ring as shown by the structure below

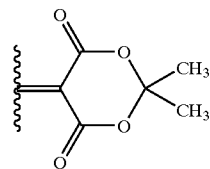

W is O or a chemical bond or a pharmaceutically acceptable salt thereof.

Further preferred compounds are those of Formula I wherein:

A and B are independent substituents from the group including S, CH or N;

provided that when A is S, B is CH or N; and when B is S, A is CH or N; and

A and B cannot both be CH;

$R^1 = R^2$ and are selected from the group which includes $C_1$ to $C_3$ alkyl, substituted $C_1$ to $C_3$ alkyl, or spirocyclic alkyl constructed by fusing $R^1$ and $R^2$ to form a 3 to 6 membered spirocyclic ring;

$R^3$ is H, OH, $NH_2$, $C_1$ to $C_6$ alkyl, substituted $C_1$ to $C_6$ alkyl, or $COR^C$;

RC is H, $C_1$ to $C_4$ alkyl, or $C_1$ to $C_4$ alkoxy;

$R^4$ is a disubstituted benzene ring containing the substituents X and Y as shown below:

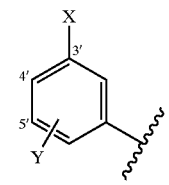

X is selected from the group including halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkyl;

Y is a substituent on the 4' or 5' position selected from the group of H, halogen, CN, $NO_2$, $C_1$ to $C_3$ alkoxy, $C_1$ to $C_4$ alkyl, or $C_1$ to $C_3$ thioalkyl; or $R^4$ is a five membered ring with the structure shown below:

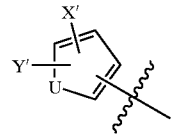

U is O, S, or $NR^5$;

$R^5$ is H, or $C_1$ to $C_3$ alkyl, or $C_1$ to $C_4$ $CO_2$alkyl;

X' is selected from halogen, CN, $NO_2$, $C_1$ to $C_3$ alkyl or $C_1$ to $C_3$ alkoxy;

Y' is H or $C_1$ to $C_4$ alkyl; or $R^4$ is a six membered ring with the structure:

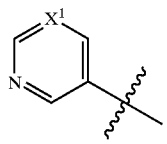

$X^1$ is N or $CX^2$,
$X^2$ is halogen, CN or $NO_2$;
Q is O, S, $NR^6$, or $CR^7R^8$;
$R^6$ is selected from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;
$R^7$ and $R^8$ are independent substituents selected from the group of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, or CN $CO_2R^9$;
$R^9$ is $C_1$ to $C_3$ alkyl; or $CR^7R^8$ comprise a six membered ring of the structure:

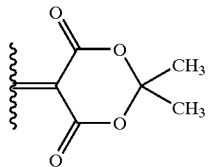

W is O or a chemical bond;
or a pharmaceutically acceptable salt thereof.

Each of the generic and subgeneric groups of compounds herein may further be divided into two further subgroups, one in which Q is oxygen and another wherein Q is selected from S, $NR^6$, or $CR^7R^5$.

The compounds of this invention have been shown to bind to the PR and act as agonists and/or antagonists in functional models, either in-vitro and/or in-vivo. These compounds may be used for contraception, in the treatment of fibroids, endometriosis, breast, uterine, ovarian and prostate cancer, osteoporosis and post menopausal hormone replacement therapy.

The compounds in the present invention contain a pendent aromatic substituent which may consist of aryl, substituted aryl, heteroaryl or substituted heteroaryl groups.

The compounds of this invention may contain an asymmetric carbon atom and some of the compounds of this invention may contain one or more asymmetric centers and may thus give rise to optical isomers and diastereomers. While shown without respect to stereochemistry in Formula I, II, and III, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having from one to 8 carbon atoms, preferably from 1 to 6 carbon atoms; "alkenyl" is intended to include both straight- and branched-chain alkyl group having from 2 to 8 carbon atoms, preferably 2 to 6 carbon atoms, with at least one carbon-carbon double bond; "alkynyl" group is intended to cover both straight- and branched-chain alkyl group having from 2 to 8 carbon atoms, preferably 2 to 6 carbon atoms, with at least one carbon-carbon triple bond.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but not limited to phenyl, naphthyl, biphenyl, anthryl, tetrahydronaphthyl, phenanthryl.

The term "substituted aryl" refers to aryl as just defined having one or more substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one or more substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups may be either same or different and the point of attachment is on the nitrogen atom. The term "thioalkyl" is used herein to refer to the SR group, where R is alkyl or substituted alkyl. The term "halogen" refers to Cl, Br, F, and I element.

The compounds of this invention can be prepared following the Schemes illustrated below:

Cyclocarbamate Derivatives

Processes for Preparing Thiophene Cyclocarbamate Derivatives

A. Methods for synthesizing the thiophene cyclocarbamate compounds depicted in Scheme 1 are described below:

Scheme 1

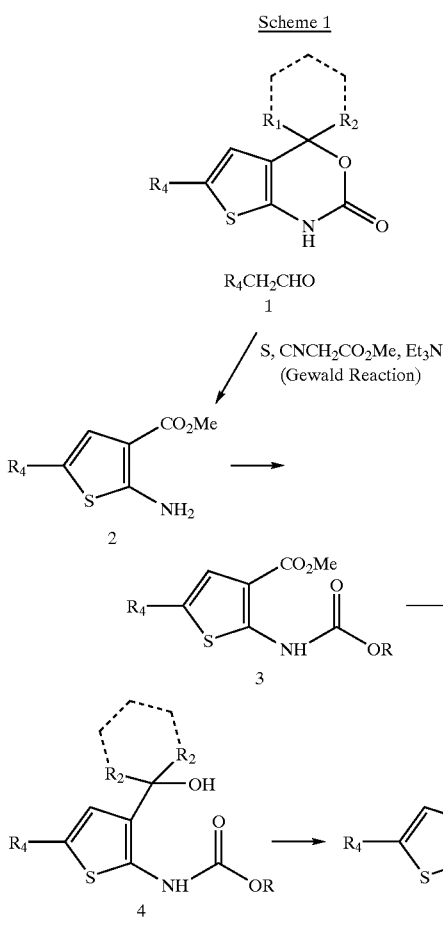

Thus the amino thiophene ester 2 was prepared according to a literature procedure involving the Gewald reaction (see Comprehensive Heterocyclic Chemistry II. A Review of the Literature 1982–1995. A. R. Katritsky et al. Vol. 2 page 639), i.e. the reaction of a suitably substituted aromatic acetaldehyde with sulfur and methyl cyanoacetate in refluxing methanol (Scheme 1). Reaction of the 2-amino group with a suitable chloroformate or carbonate affords the protected amine 3. This can be accomplished by allowing 2 to react with a chloroformate or carbonate derivative such as methyl chloroformate, ethyl chloroformate, allyl chloroformate, 2-(trimethylsilyl)ethyl chloroformate or di-tert-butyldicarbonate in a solvent such as benzene, toluene, xylene, dichloromethane, tetrahydrofuran or pyridine. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Treatment of the protected amino compound 3 with an organo-metallic reagent such as a Grignard reagent, an alkyl or aryl-zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 4. Compound 4 may then be subjected to basic conditions to effect ring closure to give the cyclocarbamate derivative 5. Suitable conditions would involve treatment of 4 with a base such as potassium hydroxide in a solvent such as ethanol or potassium t-butoxide in a solvent such as tetrahydrofuran. The reaction can be carried out in an inert atmosphere (nitrogen or argon) from 0° C. up to the reflux temperature of the solvent.

Scheme 2

Alternatively the carbamate protecting group present in 4 may be removed under conditions appropriate for its removal to afford 6 (Scheme 2). Subsequent ring closure of 6 with a reagent such as phosgene, carbonyldimidazole or dimethyl carbonate in an appropriate solvent (tetrahydrofuran, dichloromethane, benzene, etc.) also will provide access to 5.

Scheme 3

Alternatively, compound 4 may be dehydrated to afford the isopropene derivative 7 (Scheme 3). Suitable conditions for the dehydration would be the use of a reagent such as acetic anhydride, methanesulfonyl chloride, p-toluenesulfonyl chloride or trifluoromethane sulfonyl chloride or anhydride, in a solvent such as pyridine, tetrahydrofuran, dichloromethane or benzene. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Exposure of 7 to acidic conditions would then afford ring closure to give 5. Suitable conditions would be the use of an acid such as p-toluenesulfonic acid, methanesulfonic acid or camphorsulfonic acid in a solvent such as dichloromethane, benzene, toluene or tetrahydrofuran. The reaction can be carried out under an inert atmosphere (nitrogen or argon) from 0° C. up to the reflux temperature of the solvent.

carried out in a solvent such as acetone, ethanol, benzene, toluene or tetrahydrofuran, under an inert atmosphere (nitrogen or argon) from 0° C. up to the reflux temperature of the solvent, in the presence of a palladium catalyst such as tetrakis(triphenylphosphine)palladium (0) or palladium acetate and may require an additive such as sodium carbonate, cesium fluoride or potassium phosphate.

Scheme 4

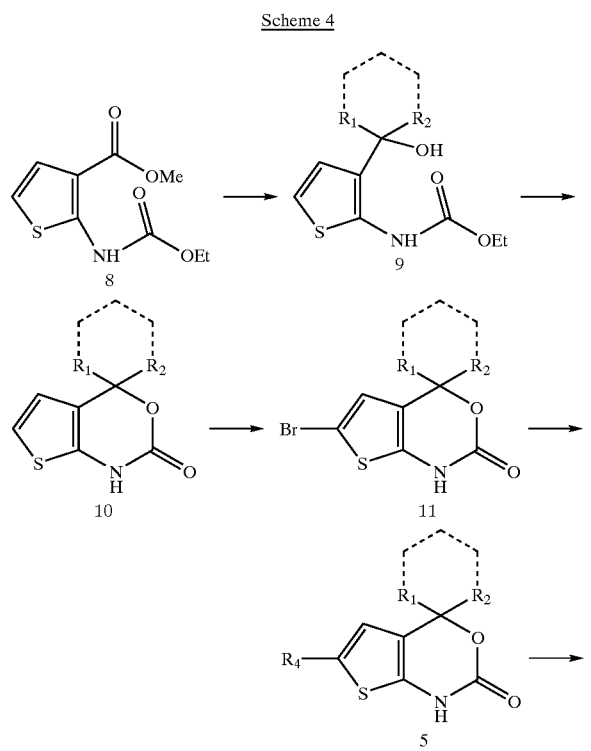

Scheme 5

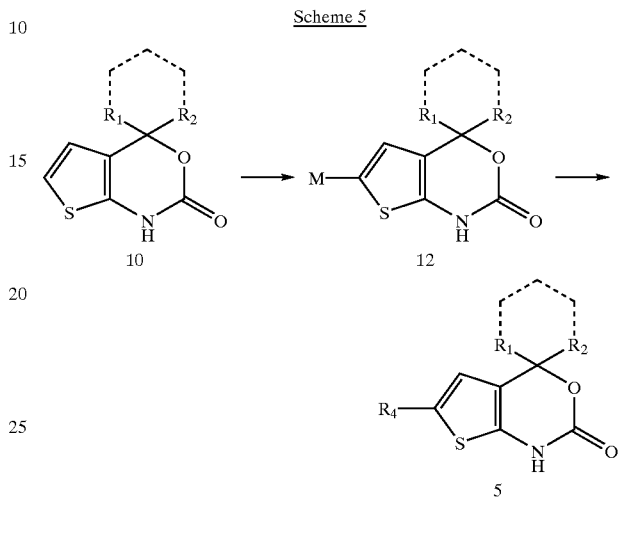

An alternative route to 5 is shown in Scheme 4. Treatment of the previously described compound 8 (M. Sugiyama, T. Sakamoto, K. Tabata, K. Endo, K. Ito, M. Kobayashi, H. Fukiumi, *Chem. Pharm. Bull.*, 37(8): 2091 (1989)) with an organo-metallic reagent such as a Grignard reagent, an alkyl or aryl zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 9. Compound 9 may then be subjected to basic conditions to effect ring closure to give the cyclocarbamate derivative 10. Suitable conditions would involve treatment of 10 with a base such as potassium hydroxide in a solvent such as ethanol or potassium t-butoxide in a solvent such as tetrahydrofuran. The reaction can be carried out in an inert atmosphere (nitrogen or argon) from 0° C. up to the reflux temperature of the solvent. Compound 10 may then be converted to the brominated derivative 11. Suitable conditions would be treatment with bromine or N-bromosuccinimide in a solvent such as dichloromethane, tetrahydrofuran or acetic acid. The reaction can be carried out in an inert atmosphere (nitrogen or argon) from 0° C. up to the reflux temperature of the solvent in the presence of an additive such as silica gel. Subsequent reaction of 11 with an aryl or heteroaryl boronic acid, boronic acid anhydride or trialkyl stannane then provides access to the desired biaryl compound 5. The reaction can be Alternatively, 10 (Scheme 5) may be treated at low temperature with a reagent such as an alkyl lithium or lithium amide in an inert solvent such as tetrahydrofuran, and then converted to a boronic acid 12 (M=B(OH)$_2$) under the action of trimethyl or triisopropyl borate, or into a stannane via reaction with trimethyltin chloride or bis (trimethyltin). Subsequent reaction of 12 with an aryl or heteroaryl bromide or iodide in the presence of a palladium catalyst such as tetrakis(triphenylphosphine) palladium (0) or palladium acetate and may require an additive such as sodium carbonate, cesium fluoride or potassium phosphate, would then effect conversion into the desired thiophene cyclocarbamate 5.

B. Methods for synthesizing the thiophene cyclocarbamate compounds depicted in Scheme 6 are described below:

Scheme 6

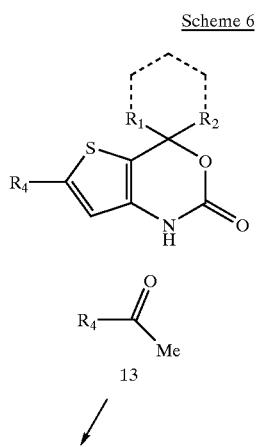

-continued

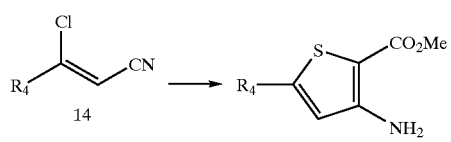

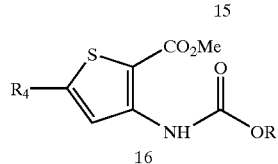

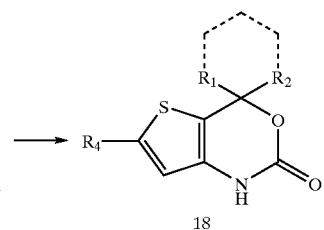

The amino thiophene compounds 15 (Scheme 6) are prepared according to a literature procedure (Comprehensive Heterocyclic Chemistry II. A Review of the Literature 1982–1995. A. R. Katrisky et al., Vol. 2, page 639) which involves treating a suitably substituted aromatic methyl ketone 13 with phosphorus oxychloride in N,N-dimethyl formamide to afford the chloro cyano olefin derivative 14. Allowing 14 to react with methyl mercaptoacetate in methanol containing sodium methoxide affords the key aminothiophene carboxylate starting material. Reaction of the 2-amino group with a suitable chloroformate or carbonate affords the protected amine 16. This can be accomplished by allowing 15 to react with a chloroformate or carbonate derivative such as methyl chloroformate, ethyl chloroformate, allyl chloroformate, 2-(trimethylsilyl)ethyl chloroformate or di-tert-butyldicarbonate in a solvent such as benzene, toluene, xylene, dichloromethane, tetrahydrofuran or pyridine. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Treatment of the protected amino compound 16 with an organometallic reagent such as a Grignard reagent, an alkyl or aryl-zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 17. Compound 17 may then be subjected to basic conditions to effect ring closure to give the cyclocarbamate derivative 18. Suitable conditions would involve treatment of 4 with a base such as potassium hydroxide in a solvent such as ethanol or potassium t-butoxide in tetrahydrofuran. The reaction can be carried out in an inert atmosphere (nitrogen or argon) from 0° C. up to the reflux temperature of the solvent.

Scheme 7

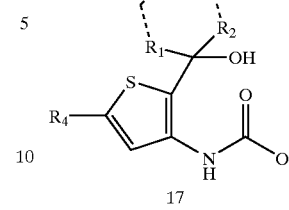

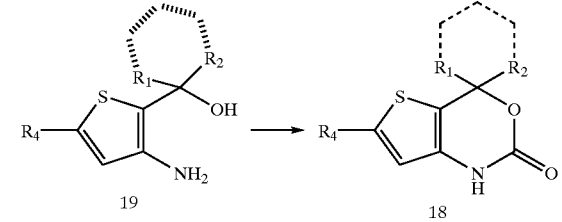

Alternatively the carbamate protecting group present in 17 may be removed under conditions appropriate for its removal to afford 19 (Scheme 7). Subsequent ring closure of 19 with a reagent such as phosgene, carbonyldiimidazole or dimethyl carbonate in an appropriate solvent (tetrahydrofuran, dichloromethane, benzene, etc.) also will provide access to 18.

Scheme 8

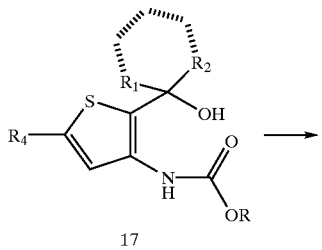

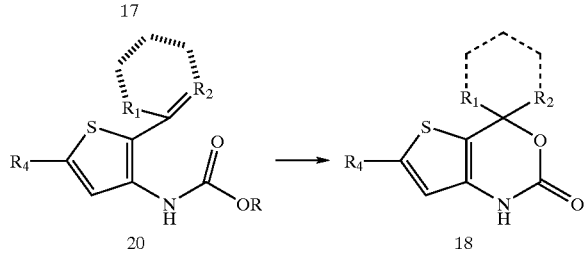

Alternatively, compound 17 may be dehydrated to afford the isopropene derivative 20 (Scheme 8). Suitable conditions for the dehydration would be the use of a reagent such as acetic anhydride, methanesulfonyl chloride, p-toluenesulfonyl chloride or trifluoromethane sulfonyl chloride or anhydride, in a solvent such as pyridine, tetrahydrofuran, dichloromethane or benzene. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Exposure of 20 to acidic conditions would then afford ring closure to give 18. Suitable conditions would be the use of an acid such as p-toluenesulfonic acid, methanesulfonic acid or camphorsulfonic acid in a solvent such as dichloromethane, benzene, toluene or tetrahydrofuran. The reaction can be carried out under an inert atmosphere (nitrogen or argon) from 0° C. up to the reflux temperature of the solvent.

Scheme 9

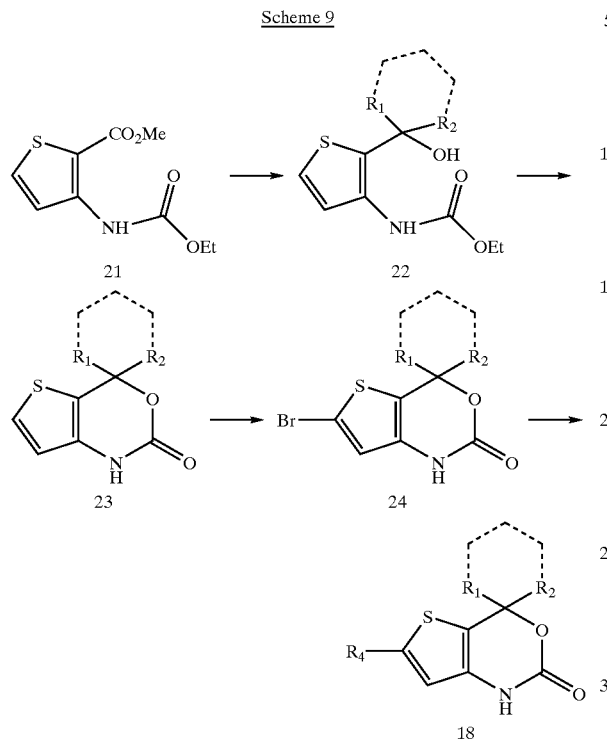

An alternative route to 18 is shown in Scheme 9. Treatment of the previously described compound 21, as taught by H. Fukiumi, M. Sugiyama, T. Sakamoto, *Chem. Pharm. Bull.*, 37(5):1197 (1989), with an organo-metallic reagent such as a Grignard reagent, an alkyl or aryl zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 22. Compound 22 may then be subjected to basic conditions to effect ring closure to give the cyclocarbamate derivative 23. Suitable conditions would involve treatment of 22 with a base such as potassium hydroxide in a solvent such as ethanol or potassium t-butoxide in tetrahydrofuran. The reaction can be carried out in an inert atmosphere (nitrogen or argon) from 0° C. up to the reflux temperature of the solvent. Compound 23 may then be converted to the brominated derivative 24. Suitable conditions would be treatment with bromine or N-bromosuccinimide in a solvent such as dichloromethane, tetrahydrofuran or acetic acid. The reaction can be carried out in an inert atmosphere (nitrogen or argon) from 0° C. up to the reflux temperature of the solvent in the presence of an additive such as silica gel. Subsequent reaction of 24 with an aryl or heteroaryl boronic acid boronic acid anhydride or trialkyl stannane then provides access to the desired biaryl compound 18. The reaction can be carried out in a solvent such as acetone, ethanol, benzene, toluene or tetrahydrofuran, under an inert atmosphere (nitrogen or argon) from 0° C. up to the reflux temperature of the solvent, in the presence of a palladium catalyst such as tetrakis (triphenylphosphine)palladium (0) or palladium acetate and may require an additive such as sodium carbonate, cesium fluoride or potassium phosphate.

Scheme 10

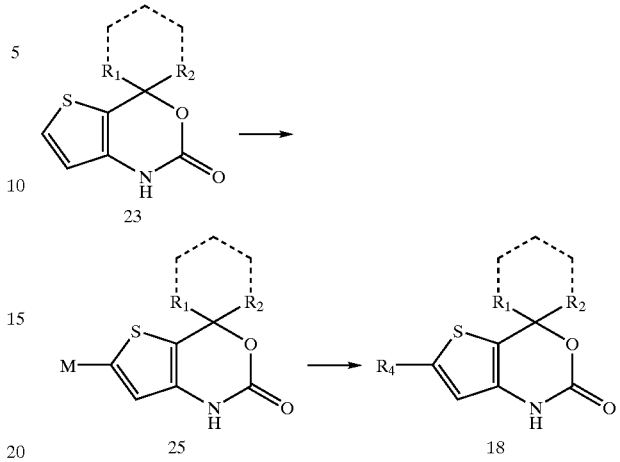

Alternatively, 23 (Scheme 10) may be treated at low temperature with a reagent such as an alkyl lithium or lithium amide in an inert solvent such as tetrahydrofuran, and then converted to a boronic acid 25 (M=B(OH)$_2$) under the action of trimethyl or triisopropyl borate, or into a stannane via reaction with trimethyltin chloride or bis (trimethyltin). Subsequent reaction of 25 with an aryl or heteroaryl bromide or iodide in the presence of a palladium catalyst such as tetrakis(triphenylphosphine) palladium (0) or palladium acetate and may require an additive such as sodium carbonate, cesium fluoride or potassium phosphate, would then effect conversion into the desired thiophene cyclocarbamate 18.

C. Method for synthesizing the thiophene thiocyclocarbamate compounds 26 and 27 depicted in Scheme 11 are described below:

Scheme 11

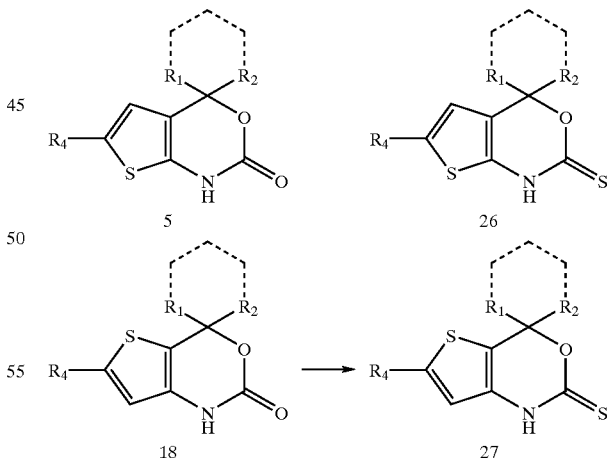

Thiophene thiocyclocarbamates 26 and 27 may be obtained directly by treating 5 and 18 respectively with phosphorus pentasulfide in refluxing pyridine. Alternatively 5 and 18 may be treated with Lawesson's reagent ([2,4-bis (4-methoxyphenyl)-1,3-dithia-2,4-diphosphetane-2,4-disulfide]) in refluxing pyridine to afford 26 and 27, respectively.

Process for Making Thiazole Cyclocarbamate Derivatives.

Methods for preparing the thiazole cyclocarbamate compounds are described below.

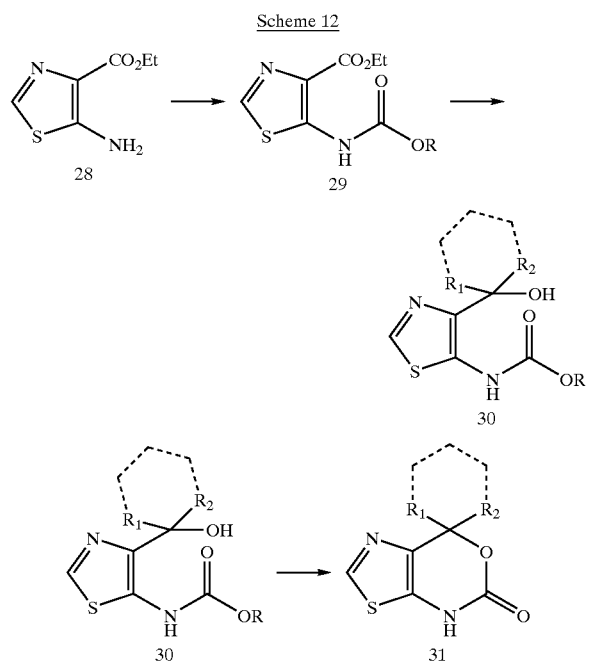

Thus the thiazole 28 was prepared according to a literature procedure, scheme 12 by B. Golankiewicz and P. Januszczyk, *Tetrahedron*, 41:5989 (1985). Reaction of the amine 28 with a suitable chloroformate or carbonate then gives the protected amine 29. This may be accomplished by reacting compound 28 with a chloroformate or carbonate derivative such as methylchloroformate, ethylchloroformate, allylchloroformate, 2-(trimethylsilyl) ethylchloroformate or di-tert-butyldicarbonate in a solvent such as dichloromethane, THF, benzene, xylene or pyridine. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylaamine. Exposure of compound 29 to an organo-metallic reagent such as a Grignard reagent, an alkyl or aryl-zinc reagent, an alkyl or aryl lithium reagent in an inert solvent (THF, diethyl ether) under an inert atmosphere (nitrogen or argon) at a suitable temperature from 0 ° C. up to the reflux temperature of the solvent will then provide the alcohol 30. Compound 30 may then be exposed to basic conditions to effect ring closure to give the cyclocarbamate derivative 31. Suitable conditions would involve treatment of compound 30 with a base such as potassium hydroxide in a solvent such as ethanol. The reaction can be carried out under an inert atmosphere (nitrogen or argon) from 0° C. up to the reflux temperature of the solvent.

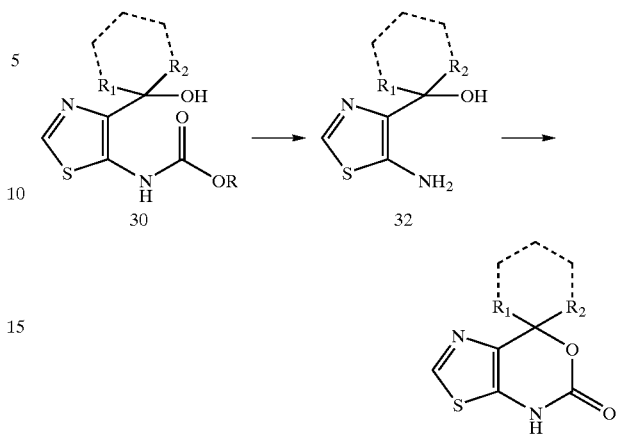

Alternatively the carbamate protecting group present in compound 30 may be removed under conditions appropriate for its removal to afford compound 32 as taught by T. W. Greene and P. G. M. Wuts, Protective Groups in Organic Synthesis, second ed., Wiley-Interscience (1991). Subsequent ring closure of compound 32 with a reagent such as phosgene, carbonyl duimidazole or dimethyl carbonate in an appropriate solvent (THF, dichloromethane, benzene, etc) will also provide access to compound 31.

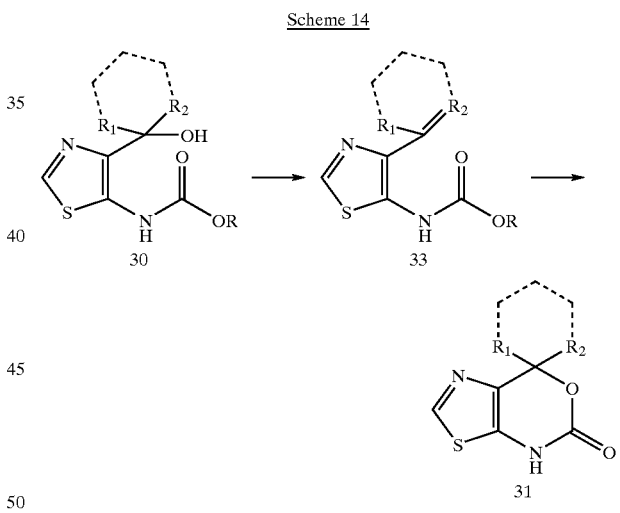

Alternatively, if compound 30 is a tertiary alcohol then it may be dehydrated to afford the isopropene derivative 33, scheme 3. Suitable conditions for the dehydration would the use of a reagent such as acetic anhydride, methanesulfonyl chloride, p-toluenesulfonyl chloride or trifluoromethane sulfonyl chloride or anhydride, in a solvent such as pyridine, THF, dichloromethane or benzene. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Exposure of compound 33 to acidic conditions would then afford ring closure to give compound 31. Suitable conditions would be the use of an acid such as p-toluenesulfonic acid, methanesulfonic acid or camphorsulfonic acid in a solvent such as dichloromethane, benzene, toluene or THF and the reaction can be carried out under an inert atmosphere (nitrogen or argon) from 0° C. up to the reflux temperature of the solvent.

Scheme 15

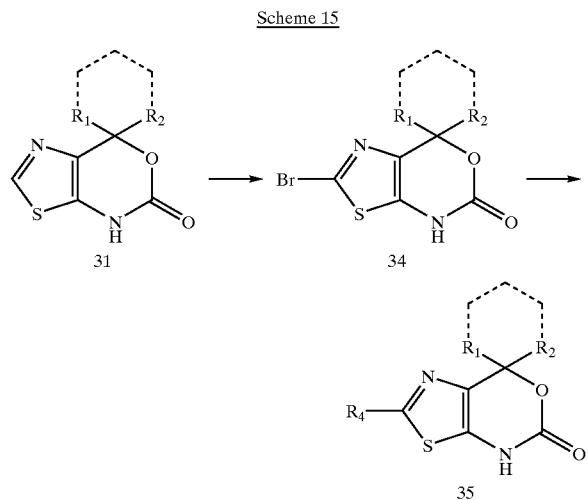

Compound 31 may then be converted into the bromide 34, scheme 15. Suitable conditions would be exposure to bromine or N-bromosuccinimide in a solvent such as dichloromethane, THF or acetic acid, the reaction can be carried out under an inert atmosphere (nitrogen or argon) from 0° C. up to the reflux temperature of the solvent in the presence of an additive such as silica gel. Subsequent reaction of compound 34 with an aryl or heteroaryl boronic acid, boronic acid anhydride or trialkyl stannane then provides access to the desired biaryl compound 35. The reaction can be carried out in a solvent such as acetone, ethanol, benzene, toluene or THF, under an inert atmosphere (nitrogen or argon) from 0° C. up to the reflux temperature of the solvent, in the presence of a palladium catalyst such as tetrakis(triphenylphosphine) palladium (0) or palladium acetate and may require an additive such as sodium carbonate, cesium fluoride or potassium phosphate.

Scheme 16

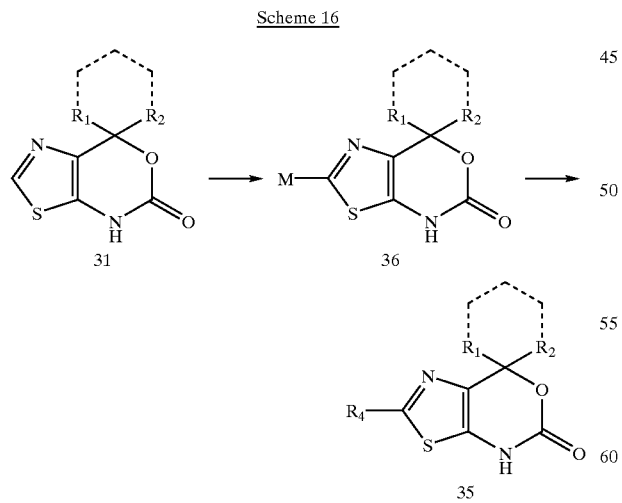

Alternatively compound 31 may be treated at low temperature with a reagent such as an alkyl lithium or lithium amide in an inert solvent such as THF, and then converted into a boronic acid (M=B(OH)$_2$) 36 under the action of trimethyl or triisopropyl borate, or into a stannane under the action of trimethyltin chloride or bis(trimethyltin), Scheme 16. Subsequent reaction with an aryl or heteroaryl bromide or iodide in the presence of a palladium catalyst such as tetrakis(triphenylphosphine) palladium (0) or palladium acetate and may require an additive such as sodium carbonate, cesium fluoride or potassium phosphate would then effect conversion into the desired compound 35.

Amide Derivatives

Process for Making Amide Thiophene Derivatives

A method for preparing thiophene derivatives is described below, scheme 17.

Scheme 17

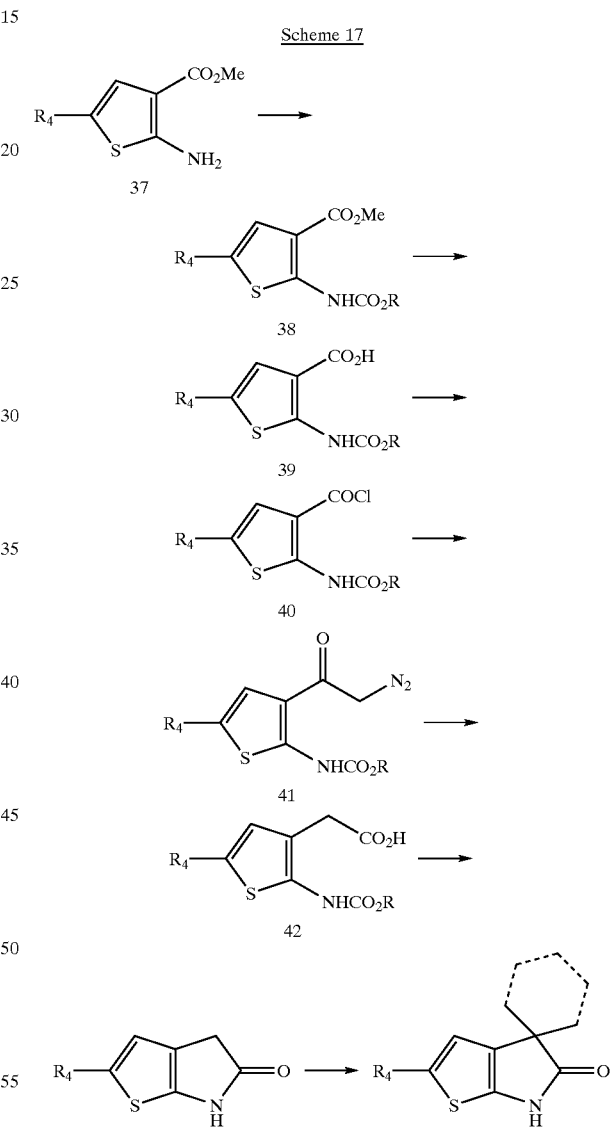

Thus the amine 37 is converted into a carbamate, such as a tert-butyl carbamate as described in scheme 1 for the preparation of compound 2. Hydrolysis of the ester 38 under basic conditions, for example lithium or sodium hydroxide in THF or methanol at room temperature then gives the acid 39. Conversion of the acid 39 into the acid chloride 40 is accomplished under standard conditions, thionyl chloride or oxalyl chloride either neat or in the presence of a solvent such as dichloromethane and an additive such as a catalytic amount of N,N-dimethylformamide. Compound 40 is then reacted with diazomethane or trimethylsilyldiazomethane in an inert solvent such as THF or dichloromethane, and the product diazoketone 41 is then rearranged in the presence of silver (I) oxide to afford the acid 42. Treatment of compound 42 under conditions that specifically remove the protecting carbamate functionality, for example acidic conditions, will then affect cyclization to give compound 43. Reaction of compound 43 with an alkylating agent such as an alkyl iodide, bromide, tosylate or mesylate, or a bis-alkyl iodide, bromide, tosylate or mesylate, under basic conditions, for example butyl lithium in the presence of N,N,N,N-tetramethylene diamine in a solvent such as THF under an inert atmosphere (nitrogen or argon) at a temperature between −78° C. and the boiling point of the solvent, will then afford the alkylated derivative 44.

Process for Making Thiazole Derivatives

A method for preparing thiazole derivatives is described below, scheme 18.

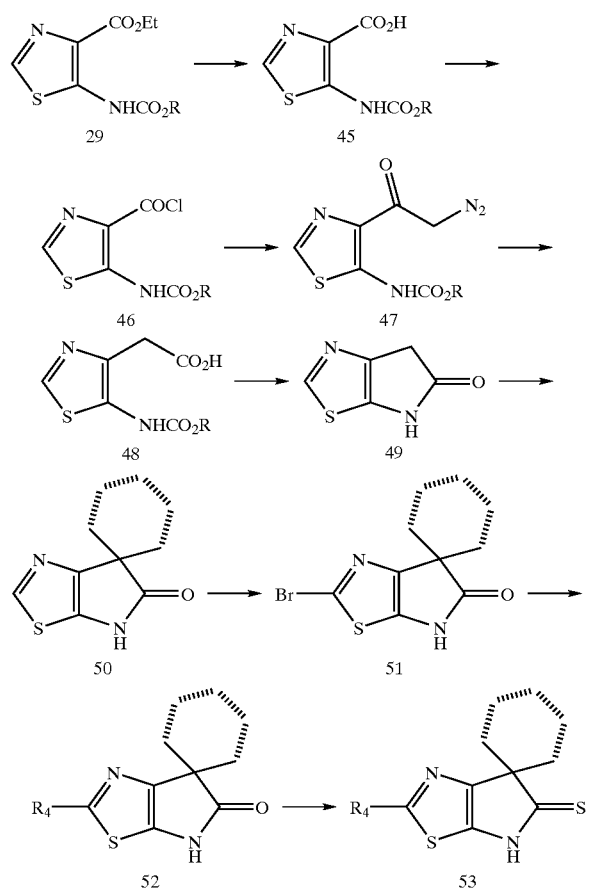

Scheme 18

Hydrolysis of the ester 29 under basic conditions, for example lithium or sodium hydroxide in THF or methanol at room temperature then gives the acid 45. Conversion of the acid 45 into the acid chloride 46 is accomplished under standard conditions, for example thionyl chloride or oxalyl chloride either neat or in the presence of a solvent such as dichloromethane and an additive such as a catalytic amount of N,N-dimethylformamide. Compound 46 is then reacted with diazomethane or trimethylsilyldiazomethane in an inert solvent such as THF or dichloromethane, and the product diazoketone 47 is then rearranged in the presence of silver (I) oxide to afford the acid 48. Treatment of compound 48 under conditions that specifically remove the protecting carbamate functionality, for example acidic conditions, will then affect cyclization to give the heterocycle 49. Reaction of compound 49 with an alkylating agent such as an alkyl iodide, bromide, tosylate or mesylate, or a bis-alkyl iodide, bromide, tosylate or mesylate, under basic conditions, for example butyl lithium in the presence of N,N,N,N-tetramethylene diamine in a solvent such as THF under an inert atmosphere (nitrogen or argon) at a temperature between −78° C. and the boiling point of the solvent, will then afford the alkylated heterocycle 50. Compound 50 may then be converted into the bromide 51. Suitable conditions would be exposure to bromine or N-bromosuccinimide in a solvent such as dichloromethane, THF or acetic acid, the reaction can be carried out under an inert atmosphere (nitrogen or argon) from 0° C. up to the reflux temperature of the solvent in the presence of an additive such as silica gel. Subsequent reaction of compound 51 with an aryl or heteroaryl boronic acid, boronic acid anhydride or trialkyl stannane then provides access to the desired biaryl compound 52. The reaction can be carried out in a solvent such as acetone, ethanol, benzene, toluene or THF, under an inert atmosphere (nitrogen or argon) from 0° C. up to the reflux temperature of the solvent, in the presence of a palladium catalyst such as tetrakis(triphenylphosphine) palladium (0) or palladium acetate and may require an additive such as sodium carbonate, cesium fluoride or potassium phosphate. The thione derivative, compound 53, may be obtained directly by treating 52 with phosphorus pentasulfide in refluxing pyridine. Alternatively 52 may be treated with Lawesson's reagent in refluxing pyridine to afford 53.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

This invention includes pharmaceutical compositions and treatments which comprise administering to a mammal a pharmaceutically effective amount of one or more compounds as described above wherein Q is oxygen as antagonists of the progesterone receptor. The invention further provides comparable methods and compositions which utilize one or more compounds herein wherein Q is S, $NR^6$, or $CR^7R^8$ as agonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of this invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

The progesterone receptor agonists of this invention, used alone or in combination, can be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

This invention also includes pharmaceutical compositions comprising one or more compounds of this invention with a pharmaceutically acceptable carrier or excipient. When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The following non-limiting examples are illustrative of exemplary compound 5.

EXAMPLE 1

6-(3-chlorophenyl)-1,4-dihydro-4,4-dimethyl-2H-thieno [2,3-d][1,3]oxazine-2-one 2-(3-Chlorobenzyl)acetaldehyde To a 25° C. solution of 3-chlorostyrene in anhydrous $CH_2Cl_2$ (10.0 g, 72.15 mmol) was added a well-stirred solution of $Pb(OAc)_4$ (35.2 g, 79.4 mmol) in trifluoroacetic acid (150 mL), dropwise. The reaction was completed within 30 min of the addition and after being stirred for a further 30 min, the mixture was poured into water, extracted with ether (3X), the combined organic layers were washed with saturated $NaHCO_3$ solution, water, dried ($MgSO_4$), and concentrated to a volume of about 15 ml and immediately used for the following reaction described below.

2-Amino-5-(3-chloro-phenyl)-thiophene-3-carboxylic acid methyl ester

To the crude aldehyde, prepared above, in methanol was added a mixture of sulfur (2.55 g, 79.44 mmol), methyl-cyanoacetate (7.88 g, 79.44 mmol), morpholine (6.92 g, 79.44) and the resulting reaction mixture was refluxed for 16 hours. The unreacted sulfur was filtered off and the filtrates were evaporated leaving behind a black residue. This residue was extracted with ether and washed with $H_2O$. Crystallized from ether/hexane (1:5) to obtain white crystals (3.85 g, 14.3 mmol, 50%), mp 85–87°. $^1$H NMR (DMSO-$d_6$) δ3.75 (s, 3H), 7.18–7.27 (m, 1H), 7.31–7.42 (m, 3H), 7.53 (s, 1H), 7.62 (s, 1H); MS(+APCI) m/z268(M+H); Anal. Calc. For $C_{12}H_{10}ClNO_2S$: C, 53.83; H, 3.76; N, 5.23. Found: C, 53.57; H, 3.37; N, 5.00.

2-Allyloxncarbonylamino-5-(3-chloro-phenyl)-thiophene-3-carboxylic acid methyl ester To a solution of 2-amino-5-(3-chloro-phenyl)-thiophene-3-carboxylic acid methyl ester (2 g, 7.5 mmol) in anhydrous 1,2-dichloroethane (50 mL) was added at room temperature under nitrogen allyl chloroformate (1.6 mL, 15.1 mmol). The reaction mixture was heated at reflux under nitrogen for 18 hours, cooled to room temperature, and treated with a saturated aqueous sodium bicarbonate solution (100 mL). The organic layer was separated and aqueous layer was extracted with methylene chloride (3×20 mL). The combined organic layers were washed (brine) and dried ($MgSO_4$). After removal of the solvent, the residue was purified by a flash silica gel column (hexane:ethyl acetate/ 7:1) to give the subtitled compound as an off-white solid (2.14 g, 81%): $^1$H-NMR (DMSO-$d_6$) δ10.2 (s, 1H), 7.73 (t, 1H, J=1.7 Hz), 7.66 (s, 1H), 7.57 (dt, 1H, J=7.7, 1.7 Hz), 7.41 (t, 1H, J=7.7 Hz), 7.34 (dt, 1H, J=6.8, 1.6 Hz), 6.01 (m, 1H), 5.41 (dd, 1H, J=7.3, 1.6 Hz), 5.29 (dd, 1H, J=10.5, 1.3 Hz), 4.74 (d, 2H, J=5.5 Hz), 3.84 (s, 3H). Anal. Calc. For $C_{16}H_{14}ClNO_4S$: C, 54.63; H, 4.01; N, 3.98. Found: C, 54.56; H, 3.92; N, 3.89.

To a solution of 2-allenoxycarbonylamino-5-(3-chloro-phenyl)-thiophene-3-carboxylic acid methyl ester (0.1 g, 0.28 mmol) in anhydrous THF was added a solution of methylmagnesium bromide (3.0 M in diethyl ether, 1.5 mL, 4.5 mmol) at room temperature under nitrogen. After stirring at room temperature under nitrogen for 20 minutes, the reaction mixture was treated with brine (10 mL) followed by addition of an aqueous 1N HCl solution (5 mL). Ethyl acetate (20 mL) was added and organic layer was separated, washed with brine (5 mL) and dried over $MgSO_4$. After removal of the solvent, the residue was purified by a flash column (silica gel, hexane:ethyl acetate/5:1) to give carbinol which was used in next step without further purification and characterization.

A mixture of above crude carbinol, potassium hydroxide (excess) in ethanol was stirred at room temperature under nitrogen overnight. The reaction solution was then acidified by an addition of a cold aqueous 1N HCl solution. Ethyl acetate (20 mL) was added and organic layer was separated, washed with brine (5 mL) and dried ($MgSO_4$). After removal of the solvent, the residue was purified by a silica gel column (hexane:ethyl acetate/2:1) to give the title compound as an off-white solid (16 mg, 19% for two steps): mp 149–150° C.; $^1$H-NMR (DMSO-$d_6$) δ10.69 (s, 1H), 7.64 (t, 1H, J=1.8 Hz), 7.49 (s, 1H), 7.47 (dt, 1H, J=7.7, 1.4 Hz), 7.39 (t, 1H, J=7.8 Hz), 7.29 (dt, 1H, J=7.8, 1.3 Hz), 1.61 (s, 6H). MS (EI) m/z 293/295 (M$^+$). Anal. Calc. For $C_{14}H_{12}ClNO_2S$: C, 57.24; H, 4.12; N, 4.77. Found: C, 57.27; H, 4.25; N, 4.66.

EXAMPLE 2

6-(3-chlorophenyl)-1,4-dihydro-4,4-dimethyl-2H-thieno[3,2-d][1,3]oxazine-2-one 3-Chloro-3-(3-chloro-phenyl)-acrylonitrile A solution of $POCl_3$ was slowly added to anhydrous DMF over a period of 20 minutes and the temperature was maintained around 30° C. 3'-Chloroacetophenone solution in anhydrous DMF was added to the above solution and the reaction temperature was allowed to rise to around 50° C. Hydroxylamine HCl was added to the reaction solution, portionwise, over 1 hour. A volume of 500 mL of water was added to form precipitate, stirred for 1 hour and precipitate was collected on a Büchner funnel, washed with $H_2O$, and dried to afford a yellow crystalline compound, mp 60–62° C. $^1$H NMR (DMSO-$d_6$) δ1.60(s, 6H), 7.30 (d, 1H, J=8.41 Hz), 7.41 (d, 1H, J=8.41 Hz), 10.47 (s, 1H); MS(+APCI)m/z 213(M+H); Anal. Calc. For $C_9H_9ClN_2O_2$: C, 50.84; H, 4.27; N, 13.17. Found: C, 50.99; H, 4.28; N, 12.98.

3-Amino-5-(3-chloro-phenyl)-thiophene-2-carboxylic acid methyl ester

Sodium pellets were slowly added to methanol solution to form NaOMe in situ, then methyl thioglycolate was added over a period of 20 minutes to the methanol solution. A solution of 3-Chloro-3-(3-chloro-phenyl)-acrylonitrile in methanol was added slowly and was brought to reflux for 1 hour. The reaction mixture was cooled to room temperature and methanol was concentrated to 100 mL and 200 mL of water was added, stirred for 30 minutes and the yellow precipitate was collected and washed with water several times to yield a yellow crystalline compound, mp 92–95° C. $^1$H NMR (DMSO-$d_6$) δ1.60 (s, 6H), 7.30 (d, 1H, J=8.41 Hz), 7.41(d, 1H, J=8.41 Hz), 10.47 (s, 1H); MS(+APCI)m/z 213(M+H); Anal. Calc. For $C_9H_9ClN_2O_2$: C, 50.84; H, 4.27; N, 13.17. Found: C, 50.99; H, 4.28; N, 12.98.

3-Allyloxycarbonylamino-5-(3-chloro-phenyl)-thiophene-2-carboxylic acid methyl ester To a solution of 3-Amino-5-(3-chloro-phenyl)-thiophene-2-carboxylic acid methyl ester (15 g, 56.0 mmol) in toluene (200 mL) was added a solution of allyl chloroformate (8.10 g, 67.2 mmol) in toluene (5.0 mL) and the resulting reaction solution was heated under reflux for 3 h. Toluene was stripped down and the crystals were collected and washed with ether/hexane to afford a yellow crystalline compound, mp 101–103° C. $^1$H NMR (DMSO-$d_6$) δ3.85 (s, 3H), 4.68–4.71 (d, 2H, J=5.46 Hz), 5.26–5.30 (dd, 1H, J=1.35, 9.84 Hz), 5.36–5.42 (dd, 1H, J=1.57, 15.68 Hz), 5.96(m, 2H), 7.50–7.52 (m, 2H), 7.67–7.71 (m, 1H), 7.79 (s, 1H), 8.10 (s, 1H); MS(+APCI) m/z 352(M+H); Anal. Calc. For $C_{16}H_{14}ClNO_4S$: C, 54.63; H, 4.01; N, 3.97. Found: C, 54.05; H, 4.17; N, 3.84.

[5-(3-Chloro-phenyl)-2-(1-hydroxy-1-methyl-ethyl)-thiophen-3-yl]-carbamic acid allyl ester To a solution of 3-Allyloxycarbonylamino-5-(3-chloro-phenyl)-thiophene-2-carboxylic acid methyl ester (5.3 g, 15.1 mmol) in anhydrous THF (30 mL) at room temperature was added a solution of 3.0M MeMgI in ether (20.1 mL, 60.24 mmol). After 30 minutes, the reaction was slowly quenched with $H_2O$ (10 mL), treated with saturated $NH_4OH$ (100 mL), extracted with ether (200 mL), washed with brine, dried ($MgSO_4$), concentrated, and chromatographed (hexane/ether, 1:4): mp 60–61° C.; $^1$H NMR (DMSO-$d_6$) δ1.52 (s, 6H), 4.59–4.61 (d, 2H, J=5.35 Hz), 5.22–5.36 (m, 2H), 5.91–6.04 (m, 2H), 7.33–7.67 (m, 5H), 8.89 (s, 1H); MS(EI) m/z 351/353(M+H); Anal. Calc. For $C_{17}H_{18}ClNO_3S$: C, 58.03; H, 5.16; N, 3.98. Found: C, 58.17; H, 5.16; N, 3.97.

6-(3-Chlorophenyl)-1,4-dihydro-4,4-dimethyl-2H-thieno[3,2-d][1,3]oxazin-2-one

To a solution of [5-(3-Chloro-phenyl)-2-(1-hydroxy-1-methyl-ethyl)-thiophen-3-yl]-carbamic acid allyl ester (0.12 g, 0.34 mmol) in anhydrous THF (5.0 mL) was added KO$^t$BU (0.076 g, 0.068 mmol) and stirred for 15 minutes, quenched with $H_2O$, and in situ crystallization was carried out by adding minimal amount of MeOH to the solution. The white crystals were collected on a Büchner funnel, mp 123–125° C. $^1$H NMR (DMSO-$d_6$) δ1.64(s, 6H), 7.05(s, 1H), 7.37–7.48(m, 2H), 7.53–7.56(s, 1H), 7.67–7.68 (m, 1H), 10.41(s, 1H); MS(EI) m/z 293/295(M+H); Anal. Calc. For $C_{17}H_{18}ClNO_3S$: C, 57.24; H, 4.12; N, 4.77. Found: C, 56.93; H, 3.92; N, 4.97.

EXAMPLE 3

Pharmacology

The progestational activity of the current invention was evaluated in the PRE-luciferase assay in CV-1 cells, described below. In-vitro potencies can be in the range 0.01 nM–10,000 nM. In vivo potencies are anticipated to be in the range 1 mg/kg to 30 mg/kg.

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium

The growth medium was as follows: DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase Assay

Stock CV-1 cells are maintained in growth medium. Co-transfection is done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 $\mu$l. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty $\mu$l of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in fill dose-response curves and the $EC_{50}$ or $IC_{50}$ values are calculated.

TABLE 1

Estimated $EC_{50}$, standard error (SE), and 95% confidence intervals (CI) for reference progestins from three individual studies

| Compound | Exp. | $EC_{50}$ (nM) | SE | 95% CI lower | 95% CI upper |
|---|---|---|---|---|---|
| Progesterone | 1 | 0.616 | 0.026 | 0.509 | 0.746 |
| | 2 | 0.402 | 0.019 | 0.323 | 0.501 |
| | 3 | 0.486 | 0.028 | 0.371 | 0.637 |
| Trimegestone | 1 | 0.0075 | 0.0002 | 0.0066 | 0.0085 |
| | 2 | 0.0081 | 0.0003 | 0.0070 | 0.0094 |
| | 3 | 0.0067 | 0.0003 | 0.0055 | 0.0082 |

TABLE 2

Estimated $IC_{50}$, standard error (SE), and 95% confident interval (CI) for the antiprogestin, RU486 from three individual studies

| Compound | Exp. | IC 50 (nM) | SE | 95% CI lower | 95% CI upper |
|---|---|---|---|---|---|
| RU486 | 1 | 0.028 | 0.002 | 0.019 | 0.042 |
| | 2 | 0.037 | 0.002 | 0.029 | 0.048 |
| | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A compound having the structure:

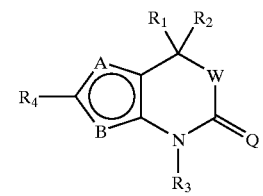

I wherein;

A and B are independent substituents selected from the group consisting of S and CH; wherein
  (i) when A is S, B is CH;
  (ii) when B is S, A is CH;
  (iii) A and B cannot both be CH; and $R_1$ and $R_2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloakyl, substituted $C_3$ to $C_8$ cycloalkyl, aryl, substituted aryl, heterocyclic, substituted heterocyclic, $COR^A$, and $NR^BCOR^A$;

or $R_1$ and $R_2$ are fused to form:

a) a C-based saturated 3 to 8 membered spirocyclic ring;
b) a C-based 3 to 8 membered spirocyclic ring having one or more carbon-carbon double bonds; or
c) a 3 to 8 membered spirocyclic ring having in its backbone one to three heteroatoms selected from the group consisting of O, S and N;

$R^A$ is H, $C_1$ to $C_3$ alkyl substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R_3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R_4$ is (v) or (vi):

(v) a substituted benzene ring containing the substituents X, Y and Z as shown below:

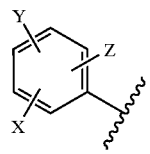

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independently selected from the group consisting of H, halogen, CN, $NO_2$, $C_1$ to $C_3$ alkoxy, $C_1$ to $C_3$ alkyl, and $C_1$ to $C_3$ thioalkyl; or (vi) a five or six membered ring having in its backbone 1, 2, or 3 heteroatoms selected from the group consisting of O, S, SO, $SO_2$ and $NR^5$, the five or six membered ring being optionally substituted by one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^G COR^F$;

$R^F$ is H, $C_1$ to $C_3$ aklyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H or $C_1$ to $C_3$ alkyl;

Q is O, S, $NR^6$, or $CR^7R^8$;

$R^6$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, and $SO_2CF_3$;

$R^7$ and $R^8$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, and $CO_2R^9$;

$R^9$ is $C_1$ to $C_3$ alkyl;

or $CR^7R^8$ may comprise a six membered ring of the structure below:

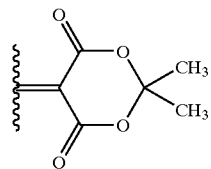

W is a bond, wherein said substituted alkyl, alkenyl, and alkynyl groups have one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

said aryl groups are selected from the group consisting of phenyl, napthyl, biphenyl, anthryl, tetrahydronaphthyl, and phenanthyl;

said substituted aryl groups have one or more substituents selected from the group consisting of halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio;

said substituted alkyloxy groups have one or more substituents selected from the group consisting of halogen, CN, OH, $NO_2$, amino, alkyl, cycloalkyl, alkenyl, alkynyl alkoxy, aryloxy, alkylcarbonyl, alkylcarboxy, alkylamino, and arylthio;

said heterocyclic group is a stable 4- to 7-membered monocyclic or a stable multicyclic heterocyclic ring having in its backbone from one to four heteroatoms selected from the group consisting of N, O, and S atoms; and said substituted heterocyclic groups have one or more substituents selected from the group consisting of halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio;

or a pharmaceutically acceptable salt thereof.

2. The compound according to claim 1 wherein:

$R_1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

$R_4$ is (vii) or (viii):

(vii) the benzene ring having the substituents X, Y and Z as shown below:

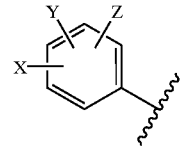

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5-membered heterocyclic ring having in its backbone 1 to 3 heteroatoms, $COR^D$, $OCOR^D$, and $NR^E COR^D$;

(viii) a five or six membered ring having in its backbone 1, 2, or 3 heteroatoms selected from the group consisting of O, S, SO, $SO_2$ and $NR^5$, the five or six membered ring being optionally substituted by one or two independent substituents selected from the group consisting of H, halogen, CN, $NO_2$, $C_1$ to $C_3$ alkyl, and $C_1$ to $C_3$ alkoxy.

3. The compound according to claim 1, wherein:

$R_1 = R_2$ and are selected from the group consisting of $C_1$ to $C_3$ alkyl and substituted $C_1$ to $C_3$ alkyl, or $R_1$ and $R_2$ are fused to form a C-based saturated 3 to 6 membered spirocyclic ring;

$R_3$ is H, OH, $NH_2$, $C_1$ to $C_6$ alkyl, substituted $C_1$ to $C_6$ alkyl or $COR^C$;

$R_4$ is (ix), (x), or (xi):

(ix) the substituted benzene ring containing the substituents X and Y as shown below:

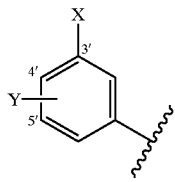

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocylic ring having in its backbone 1 to 3 heteroatoms, and $C_1$ to $C_3$ thioalkyl;

(x) the five membered ring having the stucture:

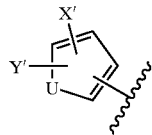

U is O, S, or $NR^5$;
$X^1$ is selected from the group consisting of halogen, CN, $NO_2$, $C_1$ to $C_3$ alkyl and $C_1$ to $C_3$ alkoxy;
Y' is H or $C_1$ to $C_3$ alkyl; or (xi) the six membered ring having the structure:

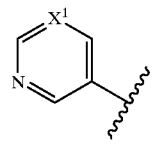

$X^1$ is N or $CX^2$,
$X^2$ is halogena CN or $NO_2$.

4. The compound according to claim 3, wherein;

$R_1 = R_2$ and are selected from the group consisting of $C_1$ to $C_3$ alkyl and substituted $C_1$ to $C_3$ alkyl.

5. The compound according to claim 3 wherein:

$R_1$ and $R_2$ are fused to form a C-based saturated 3 to 6 membered spirocyclic ring.

6. A compound having the structure:

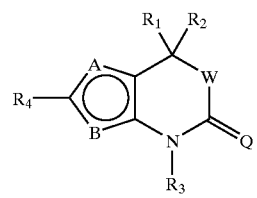

wherein:
A and B are independent substituents selected from the group consisting of S and CH; wherein;
(i) when A is S, B is CH;
(ii) when B is S, A is CH; and
(iii) A and B cannot both be CH;

$R_1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

$R_2$ is H, $C_1$ to $C_6$ alkyl, substituted $C_1$ to $C_6$ alkyl, $C_2$ to $C_6$ alkenyl substituted $C_2$ to $C_6$ alkenyl, $C_2$ to $C_6$ alkynyl, substituted $C_2$ to $C_6$ alkynyl $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

or $R_1$ and $R_2$ are fused to form:
a) a C-based saturated 3 to 8 membered spirocyclic ring,
b) a C-based 3 to 8 membered spirocyclic ring having one or more carbon-carbon double bonds; or
c) a 3 to 8 membered spirocyclic ring having in its backbone one to three heteroatoms selected from the group consisting of O, S and N;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoakyl or substituted $C_1$ to $C_4$ aminoalkyl;

$R_3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;

$R_4$ is (i) or (ii):

(i) a benzene ring having the substituents X, Y and Z as shown below:

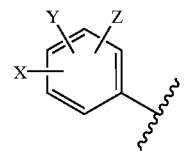

X is seleced from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5-membered heterocyclic ring having in its backbone 1 to 3 heteroatoms, $COR^D$, $OCOR^D$, and $NR^E COR^D$;

$R_D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independently selected from the group consisting of H, halogen, CN, $NO_2$, $C_1$ to $C_3$ alkoxy, $C_1$ to $C_3$ alkyl, and $C_1$ to $C_3$ thioalkyl; or (ii) a five or six membered ring having in its backbone 1, 2, or 3 heteroatoms selected from the group consisting of O, S, SO, $SO_2$ and $NR^5$, the five or six membered ring being optionally substituted by one or two independent substituents selected from the group consisting of H, halogen, CN, $NO_2$, $C_1$ to $C_3$ alkyl, and $C_1$ to $C_3$ alkoxy, $R^5$ is H or $C_1$ to $C_3$ alkyl;

Q is O, S, $NR^6$, or $CR^7R^8$;

$R^6$ is selected from the group consisting of CN, $C_1$ to $C_6$ alkyl, substituted $C_1$ to $C_6$ alkyl, $C_3$ to $C_8$ cycloalkyl substituted $C_3$ to $C_8$ cycloalkyl, aryl, substituted aryl, heterocyclic, substituted heterocyclic, and $SO_2CF_3$;

$R^7$ and $R_8$ are independent substituents selected from the group consisting of H, $C_1$ to $C_6$ alkyl, substituted $C_1$ to $C_6$ alkyl, $C_3$ to $C_8$ cycloakyl, substituted $C_3$ to $C_8$ cycloalkyl, aryl substituted aryl, heterocyclic, substituted heterocyclic, $NO_2$, CN, and $CO_2R^9$;

$R_9$ is $C_1$ to $C_3$ alkyl;

or $CR^7R^8$ may comprise a six membered ring of the structure below;

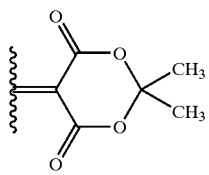

W is a bond;

wherein said substituted alkyl, alkenyl, and alkynyl groups have one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;

said aryl groups are selected from the group consisting of phenyl, Napthyl, biphenyl, anthryl, tetrahydronaphthyl, and phenanthryl;

said substituted aryl groups have one or more substituents selected from the group consisting of halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio;

said substituted alkyloxy groups have one or more substituents selected from the group consisting of halogen, CN, OH, $NO_2$, amino, alkyl, cycloalkyl, alkenyl, alkynyl, alkoxy, aryloxy, alkylcarbonyl, alkylcarboxy, alkylamino, and arylthio;

said heterocyclic group is a stable 4- to 7-membered monocyclic or a stable multicyclic heterocyclic ring having in its backbone from one to four heteroatoms selected from the group consisting of N, O, and S atoms; and said substituted heterocyclic groups have one or more substituents selected from the group consisting of halogen, CN, OH $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, and arylthio.

or a pharmaceutically acceptable salt thereof.

7. A compound having the structure:

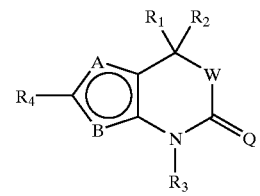

I wherein:

A and B are independent substituents selected from the group consisting of S and CH; wherein:
(i) when A is S, B is CH;
(ii) when B is S, A is CH; and
(iii) A and B cannot both be CH;

$R_1=R_2$ and are selected from the group consisting of $C_1$ to $C_3$ alkyl and substituted $C_1$ to $C_3$ alkyl or $R_1$ and $R_2$ are fused to form a C-base saturated 3 to 6 membered spirocyclic ring;

$R_3$ is H, OH, $NH_2$, $C_1$ to $C_6$ alkyl, substituted $C_1$ to $C_6$ alkyl, or $COR^C$;

$R_4$ is (i), (ii), or (iii):

(i) a substituted benzene ring containing the substituents X and Y as shown below;

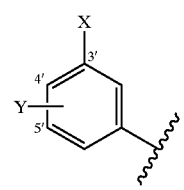

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkyl;

(ii) a five membered ring having the structure shown below:

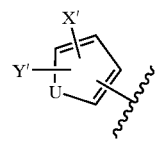

U is O, S, or $NR^5$;

X' is selected from the group consisting of halogen, CN, $NO_2$, $C_1$ to $C_3$ alkyl and $C_1$ to $C_3$ alkoxy;

Y' is H or $C_1$ to $C_4$ alkyl; or (ii) a six membered ring having the structure:

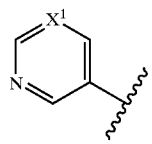

$X^1$ is N or $CX^2$,
$X^2$ is halogen, CN or $NO_2$,
Q is O, S, $NR^6$, or $CR^7R^8$;
$R^6$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, and $SO_2CF_3$;
$R^7$ and $R^8$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, and $CO_2R^9$;
$R^9$ is $C_1$ to $C_3$ alkyl;
or $CR^7R^8$ may comprise a six membered ring of the structure below:

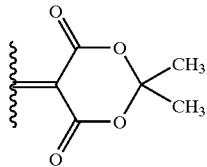

W is a bond;
wherein said substituted alkyl, alkenyl, and alkynyl groups have one or more substituents selected from the group consisting of halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio;
said aryl groups are selected from the group consisting of phenyl, Napthyl, biphenyl anthryl, tetrahydronaphthyl and phenanthryl;

said substituted aryl groups have one or more substituents selected from the group consisting of halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio;

said substituted alkloxy groups have one or more substituents selected from the group consisting of halogen, CN, OH, $NO_2$, amino, alkyl, cycloalkyl, alkenyl alkynyl, alkoxy, aryloxy, alkylcarbonyl alkylcarboxy, alkylamino, and arylthio;

said heterocyclic group is a stable 4- to 7-membered monocyclic or a stable multicyclic heterocyclic ring having in its backbone from one to four heteroatoms selected from the group consisting of N, O, and S atoms; and said substituted heterocyclic groups have one or more substituents selected from the group consisting of halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcaboxy, alkylamino, and arylthio;

or a phannaceutically acceptable salt thereof.

8. A pharmaceutical composition comprising a pharmaceutically effective amount of a compound of claim 1 and a pharmaceutically acceptable carrier or excipient.

9. A method of inducing contraception in a mammal, the method comprising administering to a mammal in need thereof a compound of claim 1.

10. A method of treatment in a mammal of a benign or malignant neoplastic disease selected from the group consisting of uterine myometrial fibroids, endometriosis, benign prostatic hypertrophy; carcinomas or adenocarcinomas of the endometrium, ovary, breast, colon, prostate, pituitary, meningioma and hormone-dependent tumors, the method comprising administering to a mammal in need thereof a compound according to claim 1, or a pharmaceutically acceptable salt thereof.

* * * * *

UNITED STATES PATENT AND TRADEMARK OFFICE
CERTIFICATE OF CORRECTION

PATENT NO. : 6,441,019 B2
DATED : August 27, 2002
INVENTOR(S) : Arthur A. Santilli et al.

It is certified that error appears in the above-identified patent and that said Letters Patent is hereby corrected as shown below:

Title page,
Item [56], FOREIGN PATENT DOCUMENTS, replace "WO 4344463" with -- DE 4344463 --.

Column 1,
Line 35, replace "MRNA" with -- mRNA --.

Column 3,
Line 55, replace "aide" with -- amide --.

Column 5,
Line 22, replace "$R^1$" with -- $R_1$ --.

Column 6,
Line 2, replace "CORD" with -- $COR^D$ --.

Column 7,
Line 39, replace "CORD" with -- $COR^D$ --.
Line 42, replace "amninoalkyl" with -- aminoalkyl --.

Column 8,
Line 29, replace "RC" with -- $R^C$ --.

Column 9,
Line 37, replace "$CR^7R^5$" with -- $CR^7R^8$ --.

Column 20,
Line 28, replace "duimidazole" with -- diimidazole --.

Column 27,
Line 14, replace "IN" with -- 1N --.

Column 28,
Line 47, replace "$KO^tBU$" with -- $K0^tBu$ --.

Column 33,
Line 46, replace "$X^1$" with -- X' --.

Column 34,
Line 43, replace "aminoakyl" with -- aminoalkyl --.

UNITED STATES PATENT AND TRADEMARK OFFICE
CERTIFICATE OF CORRECTION

PATENT NO. : 6,441,019 B2
DATED : August 27, 2002
INVENTOR(S) : Arthur A. Santilli et al.

It is certified that error appears in the above-identified patent and that said Letters Patent is hereby corrected as shown below:

Column 35,
Line 1, replace "$R_D$" with -- $R^D$ --.
Line 22, replace "$R_8$" with -- $R^8$ --.
Line 28, replace "$R_9$" with -- $R^9$ --.

Column 37,
Line 1, replace "(ii)" with -- (iii) --.

Signed and Sealed this

Eighteenth Day of February, 2003

JAMES E. ROGAN
*Director of the United States Patent and Trademark Office*